United States Patent
Warner et al.

(10) Patent No.: US 7,862,835 B2
(45) Date of Patent: Jan. 4, 2011

(54) METHOD OF MANUFACTURING A MEDICAL DEVICE HAVING A POROUS COATING THEREON

(75) Inventors: Robert Warner, Woodbury, MN (US); Michael Arney, Minneapolis, MN (US); Jesse Christian Thiesen-Toupal, White Bear Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1167 days.

(21) Appl. No.: 10/973,351

(22) Filed: Oct. 27, 2004

(65) Prior Publication Data

US 2006/0088567 A1    Apr. 27, 2006

(51) Int. Cl.
 *A61K 9/50*    (2006.01)
(52) U.S. Cl. ..................................... 424/501
(58) Field of Classification Search ........................ None
 See application file for complete search history.

(56) References Cited

U.S. PATENT DOCUMENTS

| | | | | |
|---|---|---|---|---|
| 4,764,411 | A * | 8/1988 | Courtoy et al. | 428/155 |
| 4,824,678 | A * | 4/1989 | Lindahl et al. | 424/473 |
| 5,605,696 | A * | 2/1997 | Eury et al. | 424/423 |
| 5,660,849 | A * | 8/1997 | Polson et al. | 424/426 |
| 6,180,632 | B1 * | 1/2001 | Myers et al. | 514/252.1 |
| 6,261,322 | B1 * | 7/2001 | Despres et al. | 623/23.53 |
| 6,395,300 | B1 * | 5/2002 | Straub et al. | 424/489 |
| 6,423,345 | B2 * | 7/2002 | Bernstein et al. | 424/501 |
| 6,451,348 | B1 | 9/2002 | Jeong et al. | |
| 6,599,323 | B2 * | 7/2003 | Melican et al. | 623/23.72 |
| 2001/0009688 | A1 | 7/2001 | Dinh et al. | |
| 2002/0107330 | A1 * | 8/2002 | Pinchuk et al. | 525/242 |
| 2003/0064089 | A1 * | 4/2003 | Kumar | 424/423 |
| 2003/0118649 | A1 | 6/2003 | Gao et al. | |
| 2003/0192815 | A1 * | 10/2003 | Kelly | 209/129 |
| 2003/0193104 | A1 | 10/2003 | Melican et al. | |
| 2004/0001871 | A1 * | 1/2004 | Boothman et al. | 424/423 |
| 2004/0006146 | A1 * | 1/2004 | Evans et al. | 521/50 |
| 2004/0067301 | A1 | 4/2004 | Ding | |
| 2004/0077648 | A1 * | 4/2004 | Timmer et al. | 514/241 |
| 2005/0055078 | A1 * | 3/2005 | Campbell | 623/1.11 |
| 2006/0051393 | A1 * | 3/2006 | Heruth et al. | 424/423 |

FOREIGN PATENT DOCUMENTS

| | | |
|---|---|---|
| EP | 0 734 721 A | 10/1996 |
| SU | 183373 A * | 6/1966 |

\* cited by examiner

*Primary Examiner*—Carlos A Azpuru
(74) *Attorney, Agent, or Firm*—Kenyon & Kenyon LLP

(57) ABSTRACT

Methods of manufacturing drug-coated medical devices having a porous coatings thereon. The pores are created by solid particle additives added to a mixture comprising a solvent, a drug, and a polymer to create a suspension, which is applied to the medical device. The method includes adding a surfactant to the mixture to prevent or decrease flocculation of the solid particle additives. Another method is provided that includes spraying a suspension on a medical device that comprises solid particle additives, a drug, and a polymer and analyzing the distribution of the solid particle additives in the suspension.

27 Claims, 1 Drawing Sheet

METHOD OF MANUFACTURING A MEDICAL DEVICE HAVING A POROUS COATING THEREON

FIELD OF THE INVENTION

The present invention relates to a method of manufacturing a medical device having a porous polymeric coating thereon by using solid particle additives to form the pores of the coating.

BACKGROUND OF THE INVENTION

Diffusional release of drug particles from a polymer matrix is an important and commonly used method of achieving controlled drug release. The release of drug particles from a polymer matrix is thought to occur through a network of interconnected pores, which are created by the drug particles that are initially loaded in the matrix. In particular, an aqueous medium imbibes into the matrix and dissolves the drug particles. The drug particles, once dissolved, leave behind pores in the polymer matrix and the drug particles elute through these pores. Such a release mechanism, however, is affected by particle size and loading. Specifically, drug particles may not touch each other when the drug loading is low or when the drug particles are small. Thus, with low loading or small particle size, many drug particles may be completely surrounded by polymer resulting in the drug particles being trapped in the polymer. Therefore, only those drug particles on or having a path to the surface of the matrix will be able to be released.

One method of forming a porous polymer without relying on the drug particles to create the pores is by cross-linking linear chains of monomers, such as styrene and divinylbenzene, to create very small pores within the polymer. Cross-linking, however, may have to be reduced to increase pore size. Such reduction in cross-linking may decrease the physical stability of the polymer such that the polymers cannot withstand much pressure before collapsing.

Another method of forming a porous polymer is using leachable additives to create the pores in the polymers. Leaching, however, is considered an undesirable attribute since leaching cannot be controlled and may continue after the device containing the porous polymer is deployed into the body.

Another method of forming a porous polymer where the pores are formed independent of cross-linking is to polymerize monomers in the presence of porogens, which are soluble in monomers but insoluble in formed polymers. As polymerization proceeds, pores are formed in the spaces where porogens are found. Porogens, however, may plasticize the surrounding polymer and can leach into the body thereby raising biocompatibility and toxicity concerns.

Yet another method of forming a porous polymer involves polymerizing monomers as the continuous phase in a high internal phase emulsion or foam to form cross-linked homogenous porous polymers. Emulsions and foams, however, are hard to control and the emulsion and foaming agents need to be in small quantities in order to maintain integrity.

Therefore, there is a need in the art for a method of manufacturing a porous coating for a medical device that provides greater flexibility in the amount and size of drug particles that can be loaded in the polymer matrix, provides for an improved kinetic drug release, and/or provides greater compressional strength for the porous coating.

SUMMARY OF THE INVENTION

In an embodiment, the present invention provides a method of manufacturing a medical device having a coating containing pores that are created by solid particle additives. The method includes preparing a mixture comprising a solvent, a drug, and a polymer. The method further includes dispersing the solid particle additives in the mixture to form a suspension comprising dispersed solid particle additives and applying the suspension on a medical device to form a coating containing pores on the medical device, wherein the pores are created by the solid particle additives.

In another embodiment, the present invention provides a method of manufacturing a medical device having a coating containing pores. The method comprises preparing a suspension comprising solid particle additives, a drug, and a polymer. The method further comprises spraying the suspension on a medical device to form a coating containing pores on the medical device, wherein the pores are created by the solid particle additives. The method further comprises analyzing the distribution of the solid particle additives in the suspension being sprayed on the medical device.

In certain embodiments, the solid particle additives are left in the polymer matrix for use of the device and in other embodiments, the solid particle additives are sublimed, evaporated or otherwise completely removed from the matrix prior to use of the device.

BRIEF DESCRIPTION OF THE DRAWING

The present invention will become more fully understood from the detailed description given hereinbelow and the accompanying drawing which is given by way of illustration only and wherein.

DETAILED DESCRIPTION OF THE INVENTION

Figure 1:
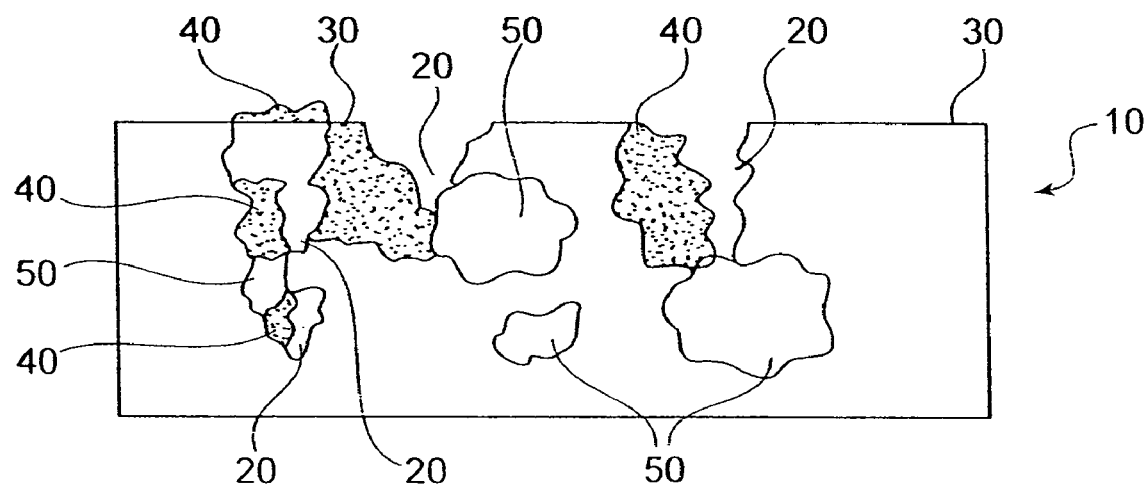
FIG. 1 is a schematic illustration of the outer surface of a medical device according to the present invention.

In general, the present invention provides methods of manufacturing a medical device having a porous coating thereon comprising a polymer matrix containing drug, wherein the pores of the coating are formed by solid particle additives to which the polymer matrix has been exposed. Such pores can also be in the form of fissures or cracks. The solid particle additives, according to the present invention, are any agents that are compatible with the drug and polymer matrix and are capable of creating a network of pores in the polymer matrix. At least a portion of the network of pores created by the solid particle additives is interconnected. This network of interconnected pores provides a continuous pathway of conducting sites that spans the polymer matrix and allows the drug access to the medium to which the medical device is exposed. Such access allows the drug to elute out of the polymer and prevents or decreases the amount of drug that is isolated or trapped within the polymer matrix. Furthermore, the addition of solid particle additives to the polymer may influence the nucleation of the drug particles promoting clustering of the drug particles in the vicinity of the solid particle additives and therefore the clustering in the vicinity of the corresponding pores created by the solid particle additives. Moreover, the pores in the polymer allow for approximately zero order drug release as the pores facilitate a uniform and constant rate of drug elution. In embodiments where the solid particle additives remain in the porous coating, the use of such additives also creates a particle-reinforced composite that increases the compressional strength of the coating.

In an embodiment, a method of manufacturing a medical device according to the present invention includes preparing a mixture comprising a solvent, a drug, and a polymer and dispersing solid particle additives in the mixture to form a suspension comprising dispersed solid particle. The solid particle additives can be dispersed by any means known to one of skill in the art including chemical and physical methods. For example, a surfactant can be added to the original drug/solvent/polymer mixture and subsequently or concurrently the solid particle additives can be added to the mixture to form a suspension. The surfactant acts to prevent or decrease flocculation of the solid particle additives such that when the suspension is applied to a medical device, there is substantially uniform distribution of solid particle additive throughout the coating. The surfactant added to the original mixture can be any biocompatible surfactant such as, for example, TWEEN 80® (polysorbate 80), TWEEN 86® (polysorbate 86), TWEEN 20® (polysorbate 20), and oleic acid.

The solid particle additives can also be dispersed by physically agitating the solid particle additives by any means known in the art. For example, the solid particle additives can be physically agitated by sonification, grinding, crushing, milling or by the application of ultrasound, microwave, or electrical energy in radiant or non-radiant form. In the case of milling, a rolling glass ball mill can be used to disperse the original drug/solvent/polymer mixture and subsequently or concurrently the solid particle additives can be added to the mixture to form a suspension. Similar to the chemical dispersion described above, the balls act to dissociate the solid particle additives.

The method of this embodiment of the present invention further includes applying the suspension on a medical device to form a porous coating on the medical device. The suspension may be applied to the entire outer surface of the medical device or only a portion thereof and can be applied by any method known in the art including dipping, spraying, rolling, brushing, electrostatic plating or spinning, vapor deposition, air spraying including atomized spray coating, and spray coating using an ultrasonic nozzle.

In another embodiment, the present invention provides a method of manufacturing a medical device including preparing a suspension comprising a polymer, a solvent, a drug and solid particle additives and spraying the suspension on a medical device to form a porous coating on the medical device. The method further comprises analyzing the distribution of the solid particle additives in the suspension being sprayed on the medical device. Such an analysis can be performed, for example, by phase doppler analysis to determine the distribution of the solid particle additive throughout the droplets being sprayed.

Referring to FIG. 1, in either embodiment, preferably, the solid particle additives 40 create a network of interconnecting pores 20 and at least a portion of the pores 20 communicate with the outer surface 30 of the coating 10 resulting in a network of fissures on the outer surface 30. Such a network of fissures allows the medium to which the medical device is exposed to penetrate the coating 10 and access the drug 50 within the coating 10 thereby permitting elution of the drug 50 exposed to the outer surface 30 of the coating 10 as well as elution of the drug 50 deeper within the coating 10. In a preferred embodiment, between about 10% to 100% of the drug is eluted from coating 10 of the medical device.

The porosity of the coating of the medical device can be controlled by adjusting the size and/or amount of the solid particle additive. For example, if smaller pore size is desired, then smaller particles of the solid particle additive may be used. Likewise, if larger pore size is desired, then larger particles of the solid particle additive may be used.

As mentioned previously, the solid particle additives according to the present invention may be any agents that are compatible with the drug and the polymer of the polymer matrix and are capable of creating a network of pores in the polymer matrix. The solid particle additives may be, for example, a metallic oxide, a biocompatible polymer, a biologically active or biologically compatible ceramic, a salt, an osteopromoting agent, solid drug particles insoluble in the polymer mixture, micro- and macro-polymeric spheres (Polygenetics Corp), nanoparticles of any of the above, and combinations of any of the above. Non-limiting examples of metallic oxides include titanium oxide, barium sulfate, silicon oxide, platinum oxide, and iridium oxide. Non-limiting examples of biocompatible polymers include polylactic acid, polylactide, polygalactide, and polysaccharide. Non-limiting examples of biologically active ceramics include calcium phosphates such as hydroxyapatite, sol-gel derived silica fibers, and BIOGLASS® (bioactive glass). Non-limiting examples of biologically compatible ceramics include silica and fumed silica. Non-limiting examples of osteopromoting agents (osteoinductive or osteoconductive) include cellulose-based and collagen-based materials, mixed bone morphogenic proteins, and osteoinductive demineralized bone. Non-limiting examples of salts include lithium halide salts, sodium halide salts, potassium halide salts, and calcium halide salts. The solid particle additives may also be carbon dioxide particles or non-steroid anti-inflammatory drug agents such as, for example, ibuprofen, propanoic acid derivatives, aspirin, diclofenac, sulindac, diflunisal, naproxen, indomethacin, tolmetin sodium, fenoprofen calcium, ketoprofen, piroxicam, flurbiprofen, meclofenamate sodium and, ketorolac tromethamine. Other suitable solid particle additives will be readily appreciated by one skilled in the art.

In a preferred embodiment, the solid particle additives that are used not only create pores in the polymer matrix but also lead to enhanced, synergistic properties that are associated with the solid particle additive such as, for example, greatly increased biocompatibility, or the suppression of inflammatory response within target vessels in which the medical device is inserted. For example, preferably the solid particle additive has anti-inflammatory properties to inhibit the restenotic cascade. Examples of such solid particle additives include any metal oxide or salt that is capable of breaking down hydrogen peroxide such as iridium oxide, platinum oxide, palladium oxide, ruthenium oxide, rhodium oxide, rhenium oxide, Raney cobalt, Raney nickel, and copper chromite. In embodiments where the drug is paclitaxel such solid particle additives are able to inhibit the restenotic cascade by acting as catalysts to breakdown hydrogen peroxide and other oxidants at a different step than the paclitaxel. Specifically, paclitaxel inhibits smooth muscle cell proliferation by stabilizing microtubules. Oxidants are produced by leukocytes in response to tissue damage and the presence of foreign material in the body. The production of oxidants ultimately increases the smooth muscle cell proliferation and inflammatory response. Although not wishing to be bound by theory, it is believed that oxidants do this by increasing growth factor levels released from the cells. It is possible that oxidants also increase interleukin levels causing an increase in leukocyte proliferation and activation. The presence of a catalyst that breaks down hydrogen peroxide would have the effect of inhibiting the production of growth factors and thus inhibiting the smooth muscle cell proliferation in a different way than the paclitaxel molecule.

In another preferred embodiment, the solid particle additive is BIOGLASS®. The BIOGLASS® particle creates pores in the polymer matrix but also has anti-inflammatory functions because the body recognizes the particle to be its own tissue. Accordingly, there is less leukocyte recruitment and activation around the inserted medical device, which is thought to decrease the amount of growth factor produced, which is thought to decrease the amount of smooth muscle cell proliferation.

The drug that is applied to the medical device may be any pharmaceutically acceptable therapeutic agents such as non-genetic therapeutic agents, biomolecules, small molecules, or cells.

Exemplary non-genetic therapeutic agents include anti-thrombogenic agents such as heparin, heparin derivatives, prostaglandin (including micellar prostaglandin El), urokinase, and PPack (dextrophenylalanine proline arginine chloromethylketone); anti-proliferative agents such as enoxaprin, angiopeptin, sirolimus (rapamycin), tacrolimus, everolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estradiol, sulfasalazine, acetylsalicylic acid, mycophenolic acid, and mesalamine; anti-neoplastic/anti-proliferative/anti-mitotic agents such as paclitaxel, cladribine, 5-fluorouracil, methotrexate, doxorubicin, daunorubicin, cyclosporine, cisplatin, vinblastine, vincristine, epothilones, endostatin, trapidil, and angiostatin; anti-cancer agents such as antisense inhibitors of c-myconcogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis (2-aminoethyl)ethyleneglycol-N,N,N',N'-tetraacetic acid and mixtures thereof; antibiotics such as gentamycin, rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, dicumarol, aspirin, prostaglandin inhibitors, platelet inhibitors and tick antiplatelet factors; vascular cell growth promoters such as growth factors, transcriptional activators, and translational promoters vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1) and bone morphogenic proteins ("BMPs"), such as, for example, BMP-2, BMP-3, BMP-4, BMP-5, BMP-6(Vgr-1), BMP-7(OP-1), BMP-8, BMP-9, BMP-10, BMP-11, BMP-12, BMP-13, BMP-14, BMP-15. Preferred BMPs are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNAs encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor $\alpha$ and $\beta$, platelet-derived endothelial growth factor, platelet-derived growth factor, tumor necrosis factor $\alpha$, hepatocyte growth factor, and insulin like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds having a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered.

Any of the therapeutic agents may be combined to the extent such combination is biologically compatible.

With respect to the type of polymers that may be used in the coating according to the present invention, such polymers may be biodegradable or non-biodegradable. Non-limiting examples of suitable non-biodegradable polymers include styrene-isobutylene-styrene block copolymers such as styrene-isobutylene-styrene tert-block copolymers (SIBS); polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHYDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), poly (lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

The solid particle additives and drug which are added to the polymer may be added in any particular order. For example, the drug may be initially added to the polymer, the polymer matrix then applied to the medical device and then the solid particle additives added to the polymer matrix. Alternatively, the drug and the solid particle additives are simultaneously or sequentially added to the polymer and the resulting suspension is applied to the medical device. Solvents may also be utilized in any order. For example, an initial polymer/solvent mixture can be formed and then the drug added to the polymer/solvent mixture. Alternatively, the polymer, solvent, and drug can be added simultaneously to form a mixture. The solid particle additives can be added at any point to the mixture. Furthermore, multiple types of drug, solid particle additives, polymers, and/or solvents may be utilized.

Preferably, the polymer is dissolved in a solvent to form a polymer/solvent solution and then the drug is mixed into the solution to form a solvent/polymer/drug solution. In this preferred embodiment, the solid particle additives are also mixed with a solvent to form a slurry and then the slurry is added to the polymer/solvent/drug solution. The resultant mixture is then applied to the medical device and the solvent is allowed to evaporate, which leaves the suspension on the medical device. The solid particle additives may also be allowed to evaporate away before use of the medical device such that the ultimate coating over the medical device does not contain the solid particle additives.

The porous coating is typically from about 1 to about 50 microns thick. In the case of balloon catheters, the thickness is preferably from about 1 to about 10 microns, and more preferably from about 2 to about 5 microns. Very thin polymer coatings, such as about 0.2-0.3 microns and much thicker coatings, such as more than 10 microns, are also possible. It is also within the scope of the present invention to apply multiple layers of polymer coatings onto the medical device. Such multiple layers may contain the same or different drug particles and/or the same or different polymers. Methods of choosing the type, thickness and other properties of the polymer and/or drug particles to create different release kinetics are well known to one in the art.

The medical device may also contain a radio-opacifying agent or coating or TAG-embedded article within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, gold, platinum, iridium, platinum oxide, iridium oxide and mixtures thereof.

Non-limiting examples of medical devices according to the present invention include catheters, guide wires, balloons, filters (e.g., vena cava filters), stents, stent grafts, vascular grafts, intraluminal paving systems, implants and other devices used in connection with drug-loaded polymer coatings. Such medical devices may be implanted or otherwise utilized in body lumina and organs such as the coronary vasculature, esophagus, trachea, colon, biliary tract, urinary tract, prostate, brain, and the like.

EXAMPLES

The following examples disclose methods of preparing a medical device having a porous coating thereon by preparing a suspension comprising solid particle additives and drug particles suspended in a polymer matrix and applying the suspension on a medical device to form the porous coating.

Example 1

Styrene-isobutylene-styrene (SIBS) is dissolved in a 95:5 toluene:THF solvent, and paclitaxel is added to the solution. The resultant mixture is cooled to 80° F. Carbon dioxide particles in toluene are ground with a rolling ball mill until a dry ice slurry is formed containing micronized carbon dioxide solid particles. The slurry is mixed with the SIBS/paclitaxel/toluene:THF solution, and the resultant mixture is sprayed onto a stent at −80° F. The toluene:THF solvent is evaporated away under a vacuum (10 torr) at −80° F., leaving a porous SIBS coating containing carbon dioxide particles and paclitaxel suspended therein. The stent is exposed to room temperature to allow the carbon dioxide particles to evaporate.

Example 2

Styrene-isobutylene-styrene (SIBS) is dissolved in a THF solvent, and paclitaxel is added to the solution. CABOSIL™ is added to the SIBS/paclitaxel/THF solution. The resultant suspension containing the CABOSIL™ is placed on a rolling glass ball mill until there is even dispersion of the CABOSIL™. The suspension is drawn down onto a film and the solvent is evaporated at room temperature. The film has a uniform thickness of 20 micrometers when dry. The film is then cut into many coupons of identical dimension, which contain identical amounts of paclitaxel. The coupons are put into separate vials. Eluting media is injected into each vial, which is kept at a constant temperature (50° C.). After a fixed amount of time (24 or 48 hours), the eluting media is withdrawn from the vial and run through a High Performance Liquid Chromatography (HPLC) instrument, which quantitatively measures the amount of paclitaxel in the eluting media.

The foregoing description and example have been set forth merely to illustrate the invention and are not intended as being limiting. Each of the disclosed aspects and embodiments of the present invention may be considered individually or in combination with other aspects, embodiments, and variations of the invention. For example, in embodiments where the solid particle additives are dispersed to form a suspension comprising dispersed solid particle additives, the distribution of the solid particle additives can be analyzed during the application of the suspension to the medical device. Similarly, in embodiments where the distribution of the solid particle additives in the suspension are analyzed, the solid particle additives can be dispersed in the suspension prior to application on the medical device. None of the steps of the methods of the present invention are confined to any particular order of performance. Modifications of the disclosed embodiments incorporating the spirit and substance of the invention are within the scope of the present invention.

We claim:

1. A method of manufacturing a coated medical device having a coating containing fissures, the method comprising:
providing a medical device;
preparing a mixture comprising a solvent, a drug, and a polymer;
dispersing solid particle additives in the mixture to form a suspension comprising dispersed solid particle additives;
applying the suspension on the medical device to form a coating containing fissures on the medical device; and
evaporating the solvent to shrink the coating and cause the mixture to separate from the solid particle additives, thereby creating the fissures in the coating on the medical device,
wherein the solid particle additives remain in the coating during use of the medical device in the body,
wherein the solid particle additives and the drug are not both bone morphogenic proteins, and
wherein the solid particle additives are a separate component from the drug.

2. The method of claim 1, wherein the solid particle additives are insoluble in the mixture.

3. The method of claim 1, further comprising adding a surfactant to the mixture.

4. The method of claim 3, wherein the surfactant is polysorbate 86, polysorbate 80, polysorbate 20, or oleic acid.

5. The method of claim 1, wherein dispersing the solid particle additives comprises physically agitating the solid particle additives.

6. The method of claim 1, wherein the coating comprises a network of interconnected fissures.

7. The method of claim 1, wherein the coating has an outer surface and at least a portion of the fissures are on the outer surface.

8. The method of claim 1, wherein applying the suspension comprises spraying the suspension on at least a portion of the medical device.

9. The method of claim 1, wherein the solid particle additives comprise a metallic oxide, a biocompatible polymer, a biologically active ceramic, a biologically compatible ceramic, or a salt.

10. The method of claim 9, wherein the metallic oxide is selected from the group consisting of titanium oxide, barium sulfate, silicon oxide, platinum oxide, and iridium oxide.

11. The method of claim 9, wherein the biocompatible polymer is selected from the group consisting of polylactic acid, polylactide, polygalactide, and polysaccharide.

12. The method of claim 9, wherein the biologically compatible ceramic is selected from the group consisting of silica and fumed silica.

13. The method of claim 9, wherein the biologically active ceramic is selected from the group consisting of hydroxyapatite and bioactive glass.

14. The method of claim 9, wherein the salt is selected from the group consisting of lithium halide salt, sodium halide salt, potassium halide salt, and calcium halide salt.

15. The method of claim 1, wherein the solid particle additives have anti-inflammatory properties.

16. The method of claim 15, wherein the solid particle additives are selected from the group consisting of iridium oxide, platinum oxide, palladium oxide, ruthenium oxide, rhodium oxide, rhenium oxide, Raney cobalt, Raney nickel, copper chromite, and bioactive glass.

17. The method of claim 1, wherein the solid particle additives are carbon dioxide particles.

18. The method of claim 1, wherein the solid particle additives are non-steroid anti-inflammatory drugs.

19. The method of claim 1, wherein the polymer is a block polymer.

20. The method of claim 19, wherein the block polymer is styrene-isobutylene-styrene.

21. The method of claim 1, wherein the medical device is a stent.

22. The method of claim 1, further comprising allowing the solid particle additives to evaporate after the fissures are created in the coating.

23. The method of claim 1, wherein between about 50% to 100% of the drug is released from the coating on the medical device.

24. The method of claim 1, further comprising
checking the efficiency of the coating on the medical device to release the drug by analyzing the distribution of the solid particle additives in the suspension sprayed on the medical device.

25. The method of claim 24, wherein the distribution of the solid particle additives is analyzed by phase doppler analysis.

26. The method of claim 24, wherein between 50% to 100% of drug is released from the medical device.

27. The method of claim 1, wherein the drug is chosen from the group consisting of paclitaxel, sirolimus, tacrolimus and everolimus.

* * * * *